(12) United States Patent
Moore (10) Patent No.: US 6,995,281 B2
(45) Date of Patent: Feb. 7, 2006

(54) METHODS FOR SELECTIVELY REMOVING COUNTERIONS FROM COMPOUNDS AND COMPOUNDS DERIVED FROM SUCH METHODS

(75) Inventor: Christine Moore, Glenwood, MD (US)

(73) Assignee: Pfizer, Inc., Chesterfield, MO (US)

( * ) Notice: Subject to any disclaimer, the term of this patent is extended or adjusted under 35 U.S.C. 154(b) by 0 days.

(21) Appl. No.: 10/797,350

(22) Filed: Mar. 10, 2004

(65) Prior Publication Data

US 2004/0225150 A1    Nov. 11, 2004

Related U.S. Application Data

(60) Provisional application No. 60/453,798, filed on Mar. 11, 2003.

(51) Int. Cl.
*C07C 323/00* (2006.01)

(52) U.S. Cl. .................................................. 562/557
(58) Field of Classification Search ................ 562/553, 562/554, 557
See application file for complete search history.

(56) References Cited

U.S. PATENT DOCUMENTS

| | | | |
|---|---|---|---|
| 4,818,409 A * | 4/1989 | Puetter et al. | 210/638 |
| 6,403,830 B2 | 6/2002 | Webber et al. | 562/557 |
| 2002/0019563 A1 * | 2/2002 | Webber et al. | 562/477 |

OTHER PUBLICATIONS

McInnis, I B et al; J Exp Med; 184; 1519; 1996.
Lundberg et al; Lancet; 344; 1673; 1994.
Hamid et al; Lancet; 342; 1510; 1993.

* cited by examiner

*Primary Examiner*—Paul A. Zucker
(74) *Attorney, Agent, or Firm*—Philip B. Polster, II; Charles Ashbrook (57) ABSTRACT

Methods of selectively removing counterions from compounds are disclosed. Compounds derived from the methods, such as the compound S-[2-[(1-Iminoethyl)amino]ethyl]-2-methyl-L-cysteine zwitterion with between zero and up to 2 molar equivalents of hydrochloride are also disclosed.

5 Claims, 3 Drawing Sheets

METHODS FOR SELECTIVELY REMOVING COUNTERIONS FROM COMPOUNDS AND COMPOUNDS DERIVED FROM SUCH METHODS

FIELD OF THE INVENTION

Priority is claimed from U.S. Provisional Application Ser. No. 60/453,798, filed Mar. 11, 2003 incorporated herein by reference The present invention provides novel methods for removing counterions from compounds, especially useful for preparing ionic salts from zwitterionic compounds. The present invention also comprises novel compounds useful in the treatment of disease, and more particularly a novel intermediate for preparing salts of S-[2-[(1-Iminoethyl)amino]ethyl]-2-methyl-L-cysteine, and pharmaceutical compositions thereof, for the treatment of conditions involving an inappropriate expression of nitric oxide from the inducible isoform of nitric oxide synthase. S-[2-[(1-Iminoethyl)amino]ethyl]-2-methyl-L-cysteine is described and claimed in commonly assigned U.S. Pat. No. 6,403,830, herein incorporated by reference.

BACKGROUND OF THE INVENTION

Dipolar compounds, that is to say, molecules that exhibit both one or more positive and negative formal charges within the same structure, are known as zwitterions. At a pH specific to a particular zwitterion, known as the isoelectric point (pI), the net charge of that zwitterion is zero. In aqueous solution, zwitterions are typically least soluble at the isoelectric point. In biological systems, α-amino acids are among the most common zwitterionic molecules. The simplest amino acid is glycine, which has no side groups. In acidic solutions, both the α-amino group and the carboxylic acid group of glycine are protonated. At the isoelectric point, the α-amino group is protonated, but the carboxyl group is ionized. In basic solutions, both the α-amino group and the carboxyl group are deprotonated. Some natural amino acids, such as lysine, arginine and histidine, have basic side chains, and thus undergo multiple ionization states. Most naturally occurring amino acids may be precipitated by titration with appropriate acidic or basic solutions, such as hydrochloric acid or aqueous sodium hydroxide, respectively, until the isoelectric point, and hence the lowest solubility are achieved. In addition, removal of excess cationic counterion from such a titration may be performed by adding a sufficient amount of strong base. For example, to remove hydrochloride cations from an amino acid, an amount of sodium hydroxide may be added to form the sodium salt of the amino acid.

Nitric oxide (NO) is a bioactive free radical gas produced by any one of several isoforms of the enzyme nitric oxide synthase (NOS). The physiological activity of what was later identified as NO was initially discovered in the early 1980's when it was found that vascular relaxation caused by acetylcholine is dependent on the presence of the vascular endothelium. The factor derived from the endothelium, then called endothelium-derived relaxing factor (EDRF), that mediates such vascular relaxation is now known to be NO that is generated in the vascular endothelium by one isoform of NOS. The activity of NO as a vasodilator has been known for well over 100 years. In addition, NO is the active species derived from known nitrovasodilators including amylnitrite, and glyceryltrinitrate. Nitric oxide is also an endogenous stimulator of soluble guanylate cyclase (cGMP), and thus stimulates cGMP production. When NOS is inhibited by N-monomethylarginine (L-NMMA), cGMP formation is completely prevented. In addition to endothelium-dependent relaxation, NO is known to be involved in a number of biological actions including cytotoxicity of phagocytic cells and cell-to-cell communication in the central nervous system.

The identification of EDRF as NO coincided with the discovery of a biochemical pathway by which NO is synthesized from the amino acid L-arginine by the enzyme NO synthase. There are at least three types of NO synthase as follows:

(i) a constitutive, Ca++/calmodulin dependent enzyme, located in the brain, that releases NO in response to receptor or physical stimulation;

(ii) a Ca++ independent enzyme, a 130 kD protein, which is induced after activation of vascular smooth muscle, macrophages, endothelial cells, and a number of other cells by endotoxin and cytokines; and (iii) a constitutive, Ca++/calmodulin dependent enzyme, located in the endothelium, that releases NO in response to receptor or physical stimulation.

Once expressed, inducible nitric oxide synthase (hereinafter "iNOS") generates NO continuously for long periods. Clinical studies have shown that NO production and iNOS expression are increased in a variety of chronic inflammatory diseases, such as rheumatoid and osteoarthritis (see, e.g, McInnes I. B. et al., *J. Exp. Med.* 184:1519 (1996)), inflammatory bowel disease (see, e.g, Lundberg J. O. N. et al., *Lancet* 344:1673, (1994)), and asthma (see, e.g., Hamid, Q. et al., *Lancet* 342:1510 (1993)), and iNOS is implicated as a major pathological factor in these chronic inflammatory diseases.

Thus, inhibition of excessive NO production by INOS is likely to be anti-inflammatory. However, since the production of NO from eNOS and nNOS is involved in normal physiology, it would be desirable for any NOS inhibitor that is used for treating inflammation be selective for iNOS, so that normal physiological modulation of blood pressure by eNOS-generated NO, and non-adrenergic, non-cholinergic neuronal transmission by nNOS-generated NO would remain unaffected.

With all pharmaceutical compounds and compositions, the chemical and physical stability of a drug compound is important in the commercial development of that drug substance. Such stability includes the stability at ambient conditions, especially to moisture and under storage conditions. Elevated stability at different conditions of storage is needed to predict the different possible storage conditions during the lifetime of a commercial product. A stable drug avoids the use of special storage conditions as well as frequent inventory replacement. A drug compound must also be stable during the manufacturing process which often requires milling of the drug to achieve drug material with uniform particle size and surface area. Unstable materials often undergo polymorphic changes. Therefore, any modification of a drug substance which enhances its stability profile provides a meaningful benefit over less stable substances.

Several inhibitors of iNOS have been described, such as, for example, S-[2-[(1-iminoethyl)amino]ethyl]-2-methyl-L-cysteine, which is described and claimed in commonly assigned U.S. Pat. No. 6,403,830. That compound, however, is an amorphous solid. It would be desirable, therefore, to provide a crystalline solid form of an iNOS inhibitor such as S-[2-[(1-Iminoethyl)amino]ethyl]-2-methyl-L-cysteine.

Other iNOS inhibitors compounds that are synthetic amino acid analogs that include amidine functional groups include: S-[2-[(1-Iminoethyl)amino]ethyl]-2-methyl-L-cysteine, dihydrochloride; S-[2-(ethanimidoylamino)-1-methylethyl]cysteine; (2S,5E)-2-amino-6-fluoro-7-[(1-iminoethyl)amino]-5-heptenoic acid, dihydrochloride; (S, E)-2-amino-2-methyl-6-[(1-iminoethyl)amino]-4-hexenoic acid, dihydrochloride; (2S,5Z)-2-amino-2-methyl-7-[(1-iminoethyl)amino]-5-heptenoic acid, dihydrochloride; and (2S,5E)-2-amino-2-methyl-6-fluoro-7-[(1-iminoethyl)amino]-5-heptenoic acid, dihydrochloride.

Unfortunately, traditional methods of removal of cationic counterions by titration with a strong base generally results in decomposition of the amidine functional group of these compounds.

SUMMARY OF THE INVENTION

In a broad sense, present invention is directed to a method for the removal of salt counterions from a compound using an appropriate ion exchange medium. In one embodiment, the ion exchange medium is a resin. In another embodiment, the ion exchange medium is a membrane. In another embodiment, the counterion is a cation, and the ion exchange resin is an anionic resin. In another embodiment, the counterion is an anion, and the ion exchange resin is a cationic resin. In another embodiment, the compound from which the counterion is to be removed is a zwitterion. In another embodiment, the method is performed with ion exchange resin in a single stirred vessel. In another embodiment, method is performed with ion exchange resin in several batches in a plurality of stirred vessels in series, with intermediate filtering of the resin and replacing with fresh resin. In another embodiment, the zwitterionic compound from which the counterion is to be removed is a synthetic amino acid analog. In another embodiment of the invention, the synthetic amino acid includes an amidine functional group. In another embodiment of the present invention, there is provided method of making S-[2-[(1-Iminoethyl)amino]ethyl]-2-methyl-L-cysteine zwitterion characterized by having stoichiometrically less than 0.5 equivalents of hydrochloride ion to S-[2-[(1-Iminoethyl)amino]ethyl]-2-methyl-L-cysteine, comprising obtaining a source of S-[2-[(1-Iminoethyl)amino]ethyl]-2-methyl-L-cysteine dihydrochloride, and removing sufficient hydrochloric acid to obtain the S-[2-[(1-Iminoethyl)amino]ethyl]-2-methyl-L-cysteine zwitterion having stoichiometrically less than 0.5 equivalents of hydrochloride ion to S-[2-[(1-Iminoethyl)amino]ethyl]-2-methyl-L-cysteine.

Several selective inhibitors of the inducible isoform of nitric oxide synthase have been discovered. Among these iNOS inhibitors are those compounds that are synthetic amino acid analogs that include amidine functional groups, such as, for example: S-[2-[(1-Iminoethyl)amino]ethyl]-2-methyl-L-cysteine, dihydrochloride; S-[2-(ethanimidoylamino)-1-methylethyl]cysteine; (2S,5E)-2-amino-6-fluoro-7-[(1-iminoethyl)amino]-5-heptenoic acid, dihydrochloride; (S, E)-2-amino-2-methyl-6-[(1-iminoethyl)amino]-4-hexenoic acid, dihydrochloride; (2S,5Z)-2-amino-2-methyl-7-[(1-iminoethyl)amino]-5-heptenoic acid, dihydrochloride; and (2S,5E)-2-amino-2-methyl-6-fluoro-7-[(1-iminoethyl)amino]-5-heptenoic acid, dihydrochloride. The methods of the present invention are useful in partially or completely removing salt counterions from these compounds, especially for the replacement of counterions with alternative counterions, and mixtures of counterions, for the crystallization of these compounds. The methods of the present invention are particularly suited to compounds of this type, because traditional methods of removal of cationic counterions by titration with a strong base generally results in decomposition of the amidine functional group of these compounds. The methods of the present invention are also useful in partially removing counterions from compounds. Partial removal of counterions results in stoichiometrically different proportions of counterion to compound. Thus, one embodiment of the present invention provides a method to treat a salt compound with an appropriate ion exchange medium to remove a sufficient amount of a salt counterion such that stoichiometrically less than 0.5 equivalents of the counterion to the compound remains. Another embodiment of the present invention provides a method of making S-[2-[(1-Iminoethyl)amino]ethyl]-2-methyl-L-cysteine zwitterion characterized by stoichiometrically less than 0.5 equivalents of hydrochloride ion to S-[2-[(1-Iminoethyl)amino]ethyl]-2-methyl-L-cysteine comprising obtaining a source of S-[2-[(1-Iminoethyl)amino]ethyl]-2-methyl-L-cysteine dihydrochloride, and removing sufficient hydrochloric acid to obtain the S-[2-[(1-Iminoethyl)amino]ethyl]-2-methyl-L-cysteine zwitterion having stoichiometrically less than 0.5 equivalents of hydrochloride ion to S-[2-[(1-Iminoethyl)amino]ethyl]-2-methyl-L-cysteine.

The present invention is also directed to a novel intermediate, S-[2-[(1-Iminoethyl)amino]ethyl]-2-methyl-L-cysteine, useful in the preparation of salts of S-[2-[(1-Iminoethyl)amino]ethyl]-2-methyl-L-cysteine, a process for preparing the novel intermediate compound, and methods of using said novel intermediate compound. The present intermediate compound possesses useful nitric oxide synthase inhibiting activity, and is useful in the treatment or prophylaxis of a disease or condition in which the synthesis or oversynthesis of nitric oxide forms a contributory part.

The present novel intermediate itself can be used to treat diseases involving cartilage degeneration, which takes place in certain conditions such as arthritis. Accordingly, conditions in which there is an advantage in inhibiting NO production from L-arginine include arthritic conditions such as rheumatoid arthritis, osteoarthritis, gouty arthritis, juvenile arthritis, septic arthritis, spondyloarthritis, acute rheumatic arthritis, enteropathic arthritis, neuropathic arthritis, and pyogenic arthritis. In addition, NO-induced depression of chondrocyte respiration could modulate matrix loss and secondary cartilage mineralization in arthritis, in particular osteoarthritis.

Other conditions for which the present intermediate may be useful include chronic or inflammatory bowel disease, cardiovascular ischemia, diabetes, congestive heart failure, myocarditis, atherosclerosis, migraine, glaucoma, aortic aneurysm, reflux esophagitis, diarrhea, irritable bowel syndrome, cystic fibrosis, emphysema, asthma, bronchiectasis, hyperalgesia, cerebral ischemia, thrombotic stroke, global ischemia (secondary to cardiac arrest), multiple sclerosis and other central nervous system disorders mediated by NO, for example Parkinson's disease and Alzheimer's disease. Further neurodegenerative disorders in which NO inhibition may be useful include nerve degeneration and/or nerve necrosis in disorders such as hypoxia, hypoglycemia, epilepsy, and in external wounds (such as spinal cord and head injury), hyperbaric oxygen convulsions and toxicity, dementia e.g. pre-senile dementia, and AIDS-related dementia, Sydenham's chorea, Huntington's disease, Amyotrophic Lateral Sclerosis, Korsakoffs disease, imbecility relating to a cerebral vessel disorder, sleeping disorders, schizophrenia, depression, depression or other symptoms associated with Premenstrual Syndrome (PMS), anxiety and septic shock.

The present intermediate may also be used where nitric oxide inhibition may also play a role in the treatment, such as pain including somatogenic (either nociceptive or neuropathic), both acute and chronic. The present compounds could be used in any situation that a common NSAID or opioid analgesic would traditionally be administered.

Still, other disorders that may be treated by inhibiting NO production with the present compounds include opiate tolerance in patients needing protracted opiate analgesics, and benzodiazepine tolerance in patients taking benzodiazepines, and other addictive behavior, for example, nicotine and eating disorders. The present compound may also be useful as antibacterial agents.

Further conditions in which the present intermediate may be used to inhibit NO production from L-arginine include systemic hypotension associated with septic and/or toxic shock induced by a wide variety of agents; therapy with cytokines such as TNF, IL-1 and IL-2; and as an adjuvant to short term immunosuppression in transplant therapy.

The present novel intermediate may also be useful in the treatment of ocular conditions (such as ocular hypertension retinitis uveitis), systemic lupus erythematosis (SLE), glomerulonephritis, restenosis, inflammatory sequelae of viral infections, acute respiratory distress syndrome (ARDS), oxidant-induced lung injury, IL2 therapy such as in a cancer patient, cachexia, immunosuppression such as in transplant therapy, disorders of gastrointestinal motility, sunburn, eczema, psoriasis, gingivitis, pancreatitis, damage to the gastrointestinal tract resulting from infections, cystic fibrosis, treatment to a dysfunctional immune system such as an adjuvant to short term immunosuppression in organ transplant therapy, induction of labor, adenomatous polyposis, controlling tumor growth, chemotherapy, chemoprevention and bronchitis.

The present invention is also directed to pharmaceutical compositions for the treatment of pain, asthma and other airway disorders, cancer, arthritis, ocular disorders including retinopathies and glaucoma, inflammation related disorders including irritable bowel syndrome, and other disorders in which an excessive production of nitric oxide plays a role, which comprises a therapeutically effective amount of S-[2-[(1-Iminoethyl)amino]ethyl]-2-methyl-L-cysteine together with a pharmaceutically acceptable carrier, diluent or vehicle.

Besides being useful for human treatment, this compound is also useful for veterinary treatment of companion animals, exotic animals and farm animals, including mammals, rodents, and the like. More preferred animals include horses, dogs, and cats.

DETAILED DESCRIPTION

Definitions

The term "counterion," as used herein, means an ion that is chemically associated with a compound, usually, but not necessarily, by ionic bonding.

The term "DBU" means the bicyclic amidine 1,8-diazabicyclo[5.4.0] undecene.

The term "DMSO" means dimethyl sulfoxide.

The term "fresh resin" as applied to an ion exchange resin, and can mean both previously unused ion exchange resin, as well as ion exchange resin that has been used and subsequently regenerated.

The term "HPLC" means high pressure liquid chromatography.

The term "ion exchange medium," as used herein, means a functionalized, insoluble support capable of selectively removing a counterion from a compound. Non-limiting examples of ion exchange media include ion exchange resins and ion exchange membranes.

The term "NMR" means nuclear magnetic resonance, and may apply to nuclear magnetic resonance spectroscopy.

The term "purity" herein, unless otherwise qualified, means the chemical purity of a compound, such as, for example, S-[2-[(1-Iminoethyl)amino]ethyl]-2-methyl-L-cysteine, according to conventional HPLC assay.

The term "synthetic amino acid" means an amino acid that does not normally occur in nature.

The term "synthetic amino acid analog" means a synthetic amino acid that has been further modified or rationally designed to acquire a desired property.

ILLUSTRATIVE EXAMPLES

The following illustrative examples are not intended to be limiting in scope, and should not be interpreted to limit the scope of the appended claims. While the compound illustrated in the following examples is S-[2-[(1-iminoethyl)amino]ethyl]-2-methyl-L-cysteine, the methods employed are applicable to a wide variety of compounds, are particularly useful in the partial or complete removal of counterions from linear amidine nitric oxide synthase inhibiting compounds.

A method to make S-[2-[(1-iminoethyl)amino]ethyl]-2-methyl-L-cysteine dihydrochloride is described in commonly assigned U.S. Pat. No. 6,403,830, incorporated herein by reference.

Briefly, synthesis of S-[2-[(1-iminoethyl)amino]ethyl]-2-methyl-L-cysteine dihydrochloride may be performed as in the following Example 1:

Example 1

S-[2-[(1-Iminoethyl)amino]ethyl]-2-methyl-L-cysteine, dihydrochloride

Example-1A

N-Boc-cysteamine

A 3L 4-neck RB flask was purged with nitrogen for 20 min and then charged sequentially with 2-aminoethanethiol hydrochloride (113.6 g, 1 mol), di-tert-butyl-dicarbonate (218.3 g, 1 mol) and 500 mL of toluene. The mixture was cooled with an ice-water bath and purged with nitrogen for 10 min. Sodium hydroxide (2.5N, 880 mL, 2.2 mol) was added to the stirring mixture in about 1.5 h at between 0 and 11° C. After the addition of sodium hydroxide was complete, the cooling bath was removed and the resulting reaction mixture was allowed to warm up to room temperature and stirred at ambient temperature overnight. This provided a solution of the title product.

Example-1B

The product solution of Example-1A was cooled with an-ice-water bath. A sample of chloroacetone (101.8 g, 1.1 mol) was added to the vigorously stirred reaction mixture over about 50 min at between 8 and 11° C. After the addition of chloroacetone was completed, the cooling bath was removed and the resulting reaction mixture was allowed to stir at room temperature overnight. The toluene layer was separated, washed with water (250 mL) and concentrated on a rotary evaporator at 85° C. under house vacuum followed by high vacuum to give the crude titled compound (225.7 g, 96.7%). $^1$H NMR (CDCl$_3$, 400 MHz) δ 4.95 (bs, 1H), 3.20 (m, 4H), 2.54 (t, 2H), 2.20 (s, 3H), 1.35 (s, 9H).

Example-1C

[2-[[(4-Methyl-2,5-dioxo-4-imidazolidinyl)methyl]thio]ethyl]carbamic acid, 1,1-dimethylethyl ester To a 3L 4-neck RB flask equipped with an overhead stirrer, a thermocouple and a condenser connected to an empty flask and a caustic trap, was added the product of Example- 1B (70 g, 0.3 mol), absolute ethanol (80 mL), sodium cyanide (19.1 g, 0.39 mol), ammonium carbonate (43.3 g, 0.45 mol) and water (720 mL) in this order. The 4$^{th}$ neck was closed with a stopper. The resulting reaction mixture was heated at between 67 and 68° C. for 6 h. Subsequently, the almost clear brown solution was cooled to room temperature. Upon cooling, solid began to form and the heterogeneous mixture was stirred at room temperature overnight. The reaction mixture was then acidified with 12% hydrochloric acid to pH 2 in about 1 h at between −2 and 2° C. The cold reaction mixture was stirred at pH2 for additional 30 min and then filtered. The flask was rinsed with distilled water (2×250 mL) and each rinse was used to wash the solid cake. The solid was again washed with distilled water (2×250 mL) and then air-dried for 4 days. The dry solid was triturated with 200 mL of toluene for 0.5 h. The slurry was filtered. The solid was rinsed sequentially with toluene (50 mL) and 1:4 ratio of toluene/hexane (100 mL) and then air-dried at room temperature overnight to give 83.1% yield of the titled compound, m.p. 134–136° C. $^1$H NMR (DMSO$_{d6}$, 400 MHz) δ 10.62 (s, 1H), 7.85 (s, 1H), 6.83 (m, 0.9H), 6.48 (bs, 0.1H), 3.29 (s, 2H), 2.99 (m, 2H), 2.71 (s, 2H), 2.95 (m, 2H), 1.32 (s, 9H), 1.24 (s, 3H); $^{13}$C NMR (DMSO$_{d6}$, 400 MHz), δ 178.1, 157.1, 156.1, 78.4, 63.7, 40.7, 39.4, 33.2, 28.9, 23.8.

Analysis Calcd for $C_{12}H_{21}N_3O_4S$: C, 47.51; H, 6.98; N, 13.85; S, 10.57. Found: C, 47.76; H, 6.88; N, 13.77; S, 10.75.

Example-1D

R and S-[2-[[(4-Methyl-2,5-dioxo-4-imidazolidinyl)methyl]thio]ethyl]carbamic acid, 1,1-dimethylethyl ester S enantiomer -continued R enantiomer The reaction product of Example-1C was separated into its R and S enantiomers on a Chiralpak® AD column eluting with methanol. The S isomer was the first eluting isomer followed by its R enantiomer. Both isomers were used in subsequent transformations.

S enantiomer:

[α] in MeOH at 25° C.=+43.0 (365 nm). $^1$HNMR: (400 mHz, $CD_3OD$) δ 1.49 (s, 9H), 2.05 (s, 3H), 2.65 (t, 2H), 2.9 (q, 2H, d), 3.20 (m, 2H). IR: λcm$^{-1}$=1772, 1709.

Analysis calculated for $C_{12}H_{21}N_3O_4S$ (formula weight=303.38): C, 47.51; H, 6.98; N, 13.85. Found: C, 47.39; H, 6.62; N, 13.83. M+H=304.

R enantiomer:

[α] in MeOH at 25° C.=−46.3 (365 nm). $^1$HNMR: (400 mHz, $CD_3OD$) δ 1.48 (s, 9H), 2.05 (s, 3H), 2.65 (t, 2H), 2.85 (q, 2H, d), 3.18 (m, 2H). IR: λcm$^{-1}$=1770, 1711.

Analysis calculated for $C_{12}H_{21}N_3O_4S$ (formula weight=303.38): C, 47.51; H, 6.98; N, 13.85. Found: C, 48.15; H, 7.04; N, 14.37. M+H=304.

Example-1E

S-(2-aminoethyl)-2-methyl-L-cysteine

Acid Hydrolysis Method:

A 500 mL three-necked round bottom flask equipped with a distillation condenser was charged with the R-isomer product of Example-1D (45.8 g, 150.9 mmol) and treated portion wise with 48% aq. HBr (160 mL) at room temperature with stirring. After the gas evolution ceased, the mixture was heated with a heating mantle until the pot temperature reached to 126° C. while the volatile t-butyl bromide (bp 72–74° C.) followed by a small amount of aq. HBr (approx. 15 mL) were distilled off. The distillation condenser was replaced with a reflux condenser and the mixture was heated at reflux for 30 hours. The solution was concentrated and the residue was dissolved in water (250 mL) and loaded on to a Dowex® 50WX4-200 ion-exchange resin (8.5×11 cm) and eluted with water (2L) followed by dilute aqueous ammonium hydroxide (30 mL of 28–30% ammonium hydroxide diluted to 1000 mL with water, 3 L). Fractions containing the desired product were combined, concentrated, and dried under vacuum at 75–80° C. for two hours to give 22.1 g (82%) of the title product, S-(2-aminoethyl)-2-methyl-L-cysteine, as a white solid. Proton and C-13 NMR spectra are consistent with the title product. Mp 157° C. $^1$H NMR (400 MHz, $D_2O$) δ 1.19 (3H, s), 2.53 (1H, d, J=13.6 Hz), 2.57–2.72 (2H, m), 2.92 (1H, d, J=13.6 Hz), 2.92 (2H, t, J=6.8 Hz); $^3$C NMR (100 MHz, $D_2O$) δ 24.7, 31.3, 38.9, 40.9, 59.6, 180.7.

Analysis Cald for $C_6H_{14}N_2O_2S$+0.1 $H_2O$: C, 40.02; H, 7.95; N, 15.56; S, 17.81. Found: C, 39.93; H, 7.98; N, 15.38; S, 17.70.

Base Hydrolysis Method:

To a stainless steel autoclave equipped with agitation was added 24.2 g (0.08 moles) of the R-isomer product of Example-1D. After purging the apparatus with nitrogen, 128 g (0.32 moles) of 10% caustic was added generating a solution. The autoclave was sealed and heated to 120° C. for 30 hours. After cooling to room temperature, the autoclave was vented to give 142 ml (151 g) of an aqueous solution of the sodium salt of the title product. H$^1$NMR (sample acidified with HCl and diluted with $D_2O$, 400 MHz): δ 1.47 (s,3H), 2.75 (m, 2H), 2.90 (d,1H, J=14.8 Hz), 3.06 (t, 2H, J=6.4 Hz), 3.14 (d, 1H, J=14.8 Hz). C$^{13}$NMR (sample acidified with HCl and diluted with $D_2O$, 100 MHz): δ 172.9, 60.8, 39.1, 39.0, 30.4, 22.2. MS (MS/CI-LC) M+1 179.

DBU (218 μL; 1.46 mmol) and ethyl acetimidate hydrochloride (171 mg; 1.34 mmol) were dissolved in ethanol (6 mL) in a 25 mL, one-necked, round-bottomed flask at room temperature (~20° C.). The title product of Example-1E (200 mg; 1.12 mmol) was added in one portion to this solution. The mixture was stirred until the title product of Example-1E was consumed (1–2 hours). The mixture was chilled with an ice-bath and then treated with 6 M HCl (830 μL). $^1$HNMR analysis indicated a chemical yield of 95 mole % or better. The solvent was evaporated and the title product of Example-1 was purified by reverse-phase or ion-exchange chromatography.

A 210 gm solution (containing ~20 g of the title product of Example-1E of the base hydrolysis reaction product was put into a 500 mL, three-necked, round-bottomed flask. The apparatus was equipped with a mechanical stirrer, a Dean-Stark apparatus (20 mL with a stopcock), a condenser, and a temperature controller. Water (140 mL) was distilled off from the mixture. 1-butanol (150 mL) was added to the pot and the remaining water (37 mL) was distilled azeotropically. Additional 1-butanol (13 mL) was removed by distillation until the pot temperature reached 117° C. The butanol slurry was cooled to room temperature and filtered through a pad of celite. The salts were washed with 1-butanol (2×20 mL). DBU (21.8 μL; 146 mmol) and ethyl acetimidate hydrochloride (17.1 mg; 134 mmol) were dissolved in 1-butanol (40 mL) in a 500 mL, three-necked, round-bottomed flask at room temperature. The apparatus was equipped with a mechanical stirrer, an addition funnel, and a temperature probe. The title product of Example-1E/1-butanol solution was put into the addition funnel and added to the ethyl acetimidate/DBU solution while maintaining the pot temperature below 25° C. The mixture was stirred until the starting material was consumed (2–3 hours). A solution of conc. HCl (94 mL) and water (100 mL) was put into a 1 L, three-necked, round-bottomed flask and chilled to 0° C. The apparatus was equipped with a mechanical stirrer, an addition funnel, and a temperature probe. The reaction mixture was put into the addition funnel. The reaction mixture was added to the aqueous HCl solution while maintaining the temperature below 25° C. Ethyl acetate (100 mL) was added to the solution and the layers were separated. The aqueous layer was washed once more with ethyl acetate (100 mL). $^1$HNMR analysis indicated a chemical yield of 95 mole % or better. This title product of Example-1 was purified by reverse-phase, ion-exchange chromatography, hydrophobic interaction chromatography, or combination thereof. $^1$HNMR (400 MHz, $D_2O$) δ 1.49 (3H, s), 2.08 (3H, s), 2.74 (2H, m), 2.91 (1H, d), 3.17 (1H, d), 3.35 (2H, t).

Example 2

Preparation of the Zwitterion

In an embodiment of the present invention, excess acid may be removed from the S-[2-[(1-Iminoethyl)amino]ethyl]-2-methyl-L-cysteine dihydrochloride concentrate using anion exchange resin. It was additionally discovered that the monohydrochloro, free zwitterion, or other fractional acid derivative of S-[2-[(1-Iminoethyl)amino]ethyl]-2-methyl-L-cysteine could be prepared using the anion exchange resin. The anion exchange method is preferred for preparing the monohydrochloride and the free zwitterion due to its simplicity. S-[2-[(1-Iminoethyl)amino]ethyl]-2-methyl-L-cysteine with less than 0.5 equivalents of acid and low excess salt is especially useful for pharmaceutical preparation of alternative salt forms.

Figure 1:
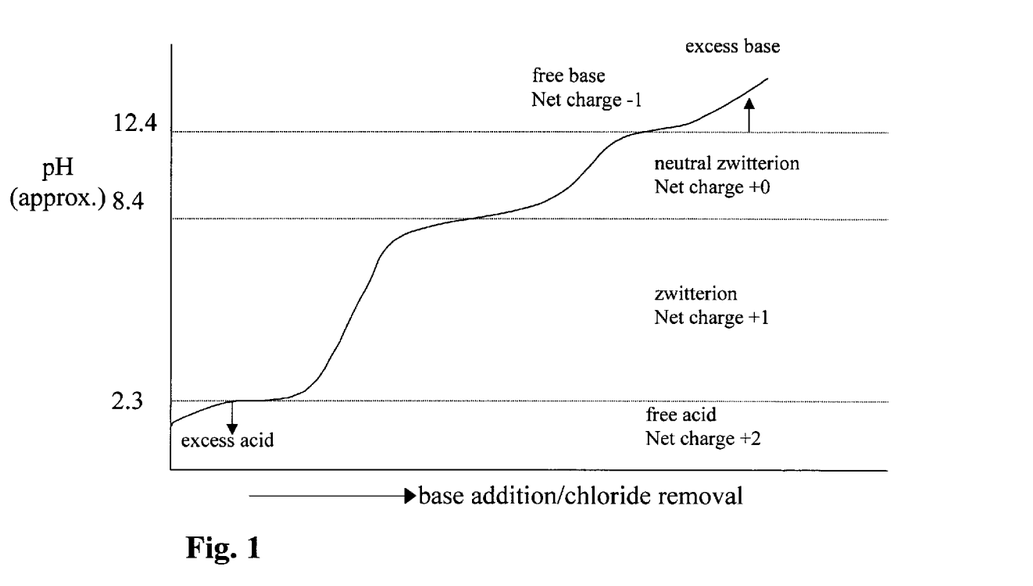
FIG. 1 is a schematic of S-[2-[(1-Iminoethyl)amino]ethyl]-2-methyl-L-cysteine titration curve, showing all ionization states.

FIG. 1 shows a schematic representation of the compound titration curve. The parent S-[2-[(1-Iminoethyl)amino]ethyl]-2-methyl-L-cysteine molecule has 3 ionizable groups and can exist in 4 ionization states.

At low pH, the molecule exists as a +2 charged free acid, with the carboxylic acid, amine and amidine moieties protonated. This is the ionization state for the dihydrochloride salt.

As the pH is increased, the carboxylic acid group is the first group to deprotonate, and this produces a net charge on the molecule of +1. If the pH increase is generated by addition of sodium hydroxide to S-[2-[(1-Iminoethyl)amino]ethyl]-2-methyl-L-cysteine, the sodium dihydrochloride salt is formed. Other bases would make their corresponding salt forms. If the increase in pH is due to removal of chloride ions by anion exchange processing, the product is the monohydrochloride salt with no sodium or other counterions.

As the pH is further increased, the amine group deprotonates (about pKa=8.4) producing the neutral zwitterionic form of the molecule. A positive charge still resides on the amidine, and a negative charge still resides on the carboxyl group. In contrast, if such material is made by the addition of sodium hydroxide to the dihydrochloride, the resulting product is the monohydrochloro sodium salt, mixed with one equivalent of sodium chloride. The material prepared by the anion exchange resin approach is the free zwitterion.

Further increases in pH lead to deprotonation of the amidine ion (pKa~12.5). The molecule in this pH range is the free base and acid salt. Note that the free base is preferably not prepared by the anion exchange method, since the negatively charged molecule binds with the anion exchange resin.

Example 3

Preparation of Free Zwitterion 60 g of Amberlite IRA400 (OH) resin (a strongly anionic quaternary ammonium polystyrene resin, about 16–50 mesh, available from Rohm & Haas, Philadelphia, Pa.,) was prewashed with 4.7 percent (by weight) ammonium hydroxide (50 ml of 28 percent ammonium hydroxide, 250 ml deionized water), followed by extensive washing with deionized water. The final conductivity was 6.1 μS.

Samples containing about 0.9 g of S-[2-[(1-Iminoethyl)amino]ethyl]-2-methyl-L-cysteine di-hydrochloride in 142 ml HCl/water solution, were concentrated on a rotary evaporator at 60° C. to an oil. To the oil, diluted to 60 ml with deionized water, was added aliquots of 0.5 g of washed anion exchange resin while stirring. At five minutes after each aliquot of resin was added, the solution pH was measured and a sample removed through a syringe filter. A total of 9 g of anion exchange resin was added. The final pH was 10.8. The resin was removed by filtration and the filtrate was concentrated to an oil by rotary evaporation at 60° C.; no solids formed. The starting material, final filtrate and all intermediate samples were assayed by HPLC and ion chromatography for chloride.

Figure 2:
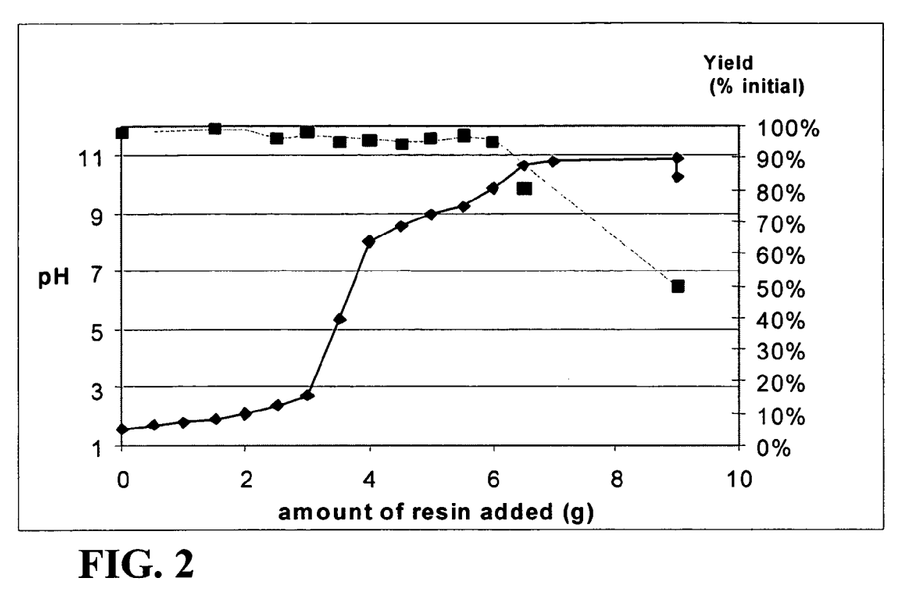
FIG. 2 is a graphical representation of titration curves of S-[2-[(1-Iminoethyl)amino]ethyl]-2-methyl-L-cysteine in water with IRA-400(OH) anion exchange resin. Diamond is pH and square (dashed line) is S-[2-[(1-Iminoethyl)amino]ethyl]-2-methyl-L-cysteine (% initial, by ion chromatography)
Figure 3:
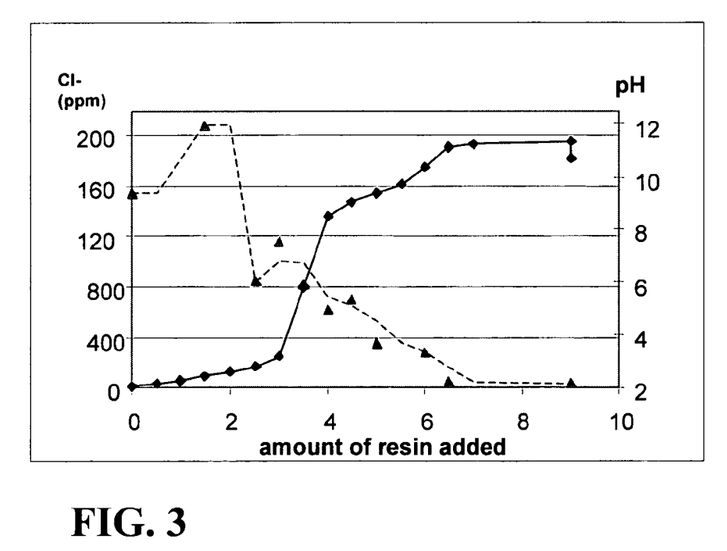
FIG. 3 is a graphical representation of titration curves of S-[2-[(1-Iminoethyl)amino]ethyl]-2-methyl-L-cysteine in water with IRA-400(OH) anion exchange resin. Diamond is pH and triangle (broken line) is chloride (by ion chromatography)

FIG. 2 shows the pseudo-titration curve for S-[2-[(1-Iminoethyl)amino]ethyl]-2-methyl-L-cysteine in water using the anion exchange resin to adjust pH. The diamond (solid line) is pH and square (dashed line) is S-[2-[(1-Iminoethyl)amino]ethyl]-2-methyl-L-cysteine (percent initial, by ion chromatography). FIG. 3 shows the pseudo-titration curve for S-[2-[(1-Iminoethyl)amino]ethyl]-2-methyl-L-cysteine in water using the anion exchange resin to adjust pH. The diamond (solid line) is pH and triangle (broken line) is chloride (by ion chromatography).

These curves are not true titration curves since samples were withdrawn during the progress of the reaction, and since true equilibrium was not attained before the increments of resin were added. Nevertheless, the graphs of FIG. 2 and FIG. 3 illustrate the expected trends. As resin is added to the S-[2-[(1-Iminoethyl)amino]ethyl]-2-methyl-L-cysteine solution the pH rises with change in slope around pH's of 2, 9 and 11. The pH's of slower rise are representative of the pK's of the carboxylic acid, amine and amidine functional groups, respectively. Above a pH of 10, the S-[2-[(1-Iminoethyl)amino]ethyl]-2-methyl-L-cysteine concentration in solution decreases. At this point, the S-[2-[(1-Iminoethyl)amino]ethyl]-2-methyl-L-cysteine is gaining a net negative charge and is binding to the resin. The chloride results show some variation between samples but in general show the trend of decreasing chloride content with increasing pH. The final chloride content is approximately 0.04 mol equivalents. HPLC assay of the samples showed no degradation.

Example 4

Removal of Excess HCl to Adjust Acid Equivalents

To 3.3 g of sample containing around 305 mg/ml S-[2-[(1-Iminoethyl)amino]ethyl]-2-methyl-L-cysteine dihydrochloride and around 0.2 eq excess HCl, was added 16.7 g of deionized water. The pH was 1.04. To 14 ml of this solution, prewashed Amberlite 400 (OH) resin was added to obtain a ph of 2.5. The anion exchange treatment lightened the color of the solution from light yellow to water white. The resin was removed by filtration and the starting material and filtrate product were analyzed by chloride titration and HPLC.

Qualitative analysis of the starting material and product by HPLC found no new peaks and no increase in impurities. The results from chloride analysis by titration show that the chloride was reduced from 2.18 equivalents to around 1.14 equivalents. Although not demonstrated here, the chloride could be adjusted to higher ratio of HCl by addition of HCl.

Example 5

Preparation of Free Zwitterion 3.3 g of a sample containing about 1 g of S-[2-[(1-Iminoethyl)amino]ethyl]-2-methyl-L-cysteine di-hydrochloride was diluted to 20 g. Aliquots of prewashed Amberlite IRA400 (OH) resin was added to the solution and samples were periodically withdrawn through a syringe filter. Intermediate resin filtrations were performed at pH of 7.1 and 8.8 by filtering off the resin in solution and then continuing to add fresh resin to the filtrate. This was done to drive the chloride removal equilibrium and minimize product adsorption. After the final pH of 11.2 was attained, the resin was filtered off. The starting materials, intermediate samples and final filtrate were analyzed.

The resulting samples were analyzed by HPLC. No difference was seen between the HPLC traces of the starting material and product at pH of 11 within a few hours. However, some degradation peaks at around 2–3 peak area % were seen in the high pH samples after storage at room temperature for around 10 days.

Example 6

Preparation of Free Zwitterion

Amberlite IRA400 (Cl) resin was rinsed with 3M HCl, water, and then 3M NaOH. Aliquots were 100 ml per 10 g of resin. This procedure was repeated 3 times in order to clean the resin and in order to generate the OH form. A final rinse with water was carried out until the conductivity of the eluting water was 2 $\mu$S. The resin was then used to titrate 40 ml of a 50 mg/ml solution of S-[2-[(1-Iminoethyl)amino]ethyl]-2-methyl-L-cysteine dihydrochloride. The concentration is expressed in terms of zwitterion equivalents. Aliquots were taken throughout the titration, filtered and analyzed by HPLC. Subsamples of the aliquots were saved for a second HPLC analysis 1 week after the titration was performed in order to assess the stability of the samples. Additional aliquots were taken for Cl analysis using an ion selective electrode. The pH was also monitored throughout the titration.

The results found in this example mirrored the results found in Example 3. The chloride specific electrode used here to measure the Cl content produced data that were much less noisy (see FIG. 4). Note that the data indicate that in removing 98% of the Cl, a pH of ~10.85 is reached. More Cl can be removed but this produced significant binding of compound to the resin (see FIG. 5). This loss of compound due to resin binding can be minimized by filtering off the resin toward the end of titration and replacing a small amount of fresh resin. This practice helps drive the equilibrium of chloride removal and minimize the sites available for compound loss by binding.

Figure 4:
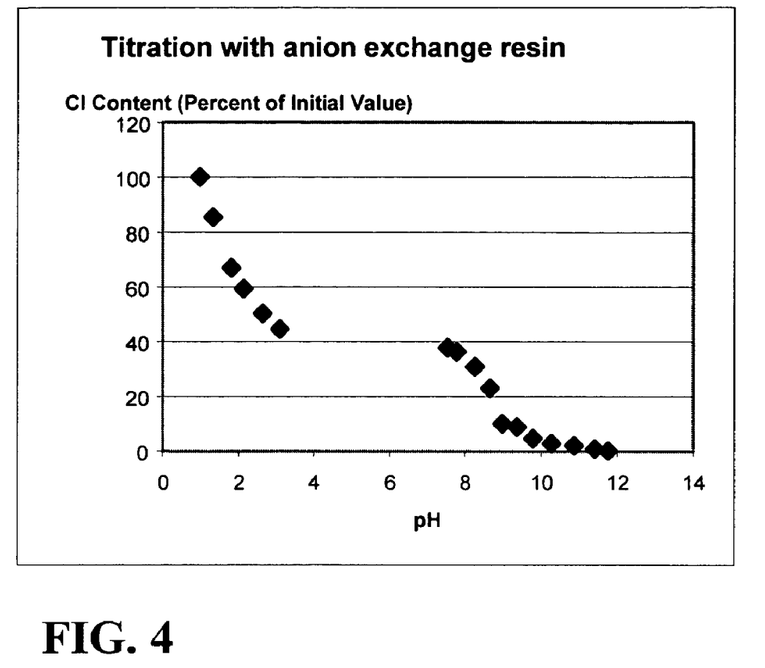
FIG. 4 Shows titration curves of S-[2-[(1-Iminoethyl)amino]ethyl]-2-methyl-L-cysteine in water with IRA-400 anion exchange resin.
Figure 5:
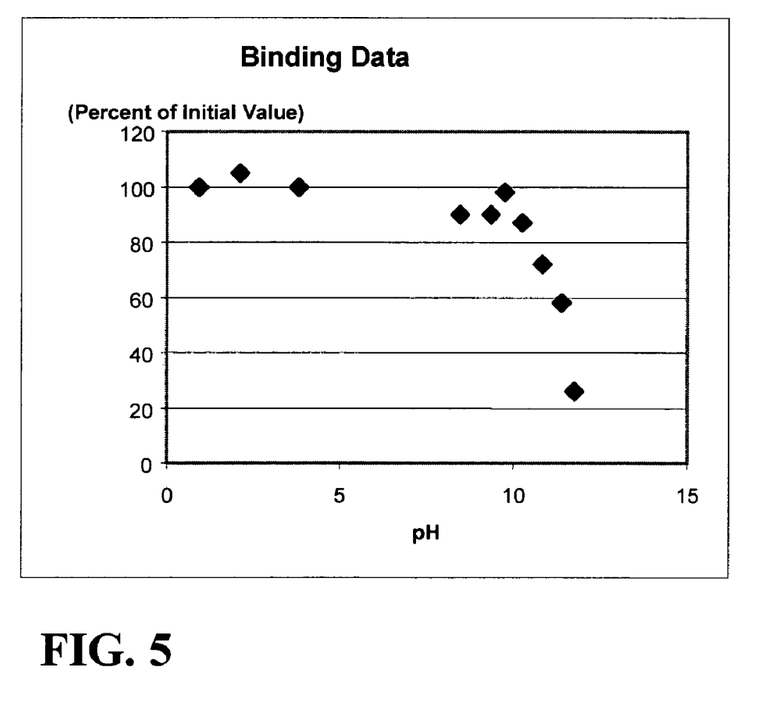
FIG. 5 shows the relevant binding data associated with increasing pH.

FIG. 4 Shows titration curves of S-[2-[(1-Iminoethyl)amino]ethyl]-2-methyl-L-cysteine in water with IRA-400 anion exchange resin. FIG. 5 shows the relevant binding data associated with increasing pH.

HPLC analyses were performed using an ion pairing gradient method. The method has been shown to detect the presence of the degradation products that are expected when S-[2-[(1-Iminoethyl)amino]ethyl]-2-methyl-L-cysteine is made basic. As can be seen in the following table, the data indicate that degradation is not immediate but instead occurs over a period of days.

TABLE 2

Stability of -[2-[(1-Iminoethyl)amino]ethyl]-2-methyl-L-cysteine free zwitterion.

| Sample pH | Purity At The Time Of Titration (Peak Area %) | Purity One Week After Titration (Peak Area %) |
|---|---|---|
| .94 | 98.0 | 98.3 |
| 2.13 | 98.6 | 98.4 |
| 3.83 | 98.7 | 98.1 |
| 8.48 | 98.5 | 97.4 |
| 9.37 | 98.5 | 97.2 |
| 9.78 | 98.3 | 97.2 |
| 10.27 | 98.3 | 96.4 |
| 10.83 | 96.6 | 94.7 |
| 11.6 | 98.3 | 92.4 |
| 11.75 | 97.9 | 89.2 |

Samples were analyzed a few hours after preparation of the free zwitterion and again after 1 week.

HPLC Method

Pump A: 20 mM $KH_2PO_4$, 10 mM Pentane sulfonic acid, adjusted to pH=3 with phosphoric acid Pump B: Acetonitrile Gradient: 0% B at 0 min, 26% B at 15 min, 0% B at 15.1 min Column: YMC ODS-AQ 120 A, 5 $\mu$m, 2.6×150 mm Wavelength=205 nm

Example 7

Removal of Excess HCl/Preparation of Monohydrochloro 2-[(1-Iminoethyl)amino]ethyl]-2-methyl-L-cysteine In these examples, the chloride removal process was run in batch by stirring the resin, but it could easily be run in a plant setting by recirculating the S-[2-[(1-Iminoethyl)amino]ethyl]-2-methyl-L-cysteine dihydrochloride solution over an anion exchange resin column or an anion exchange membrane. If the pH is inadvertently raised beyond the desired range, it may easily be adjusted back by adding an appropriate amount of HCl. It would be well within the ordinary skill in the art to design a large scale anion exchange process for this purpose.

Pharmaceutical Compositions

Also embraced within this invention is a class of pharmaceutical compositions comprising S-[2-[(1-Iminoethyl)amino]ethyl]-2-methyl-L-cysteine zwitterion in association with one or more non-toxic, pharmaceutically-acceptable carriers and/or diluents and/or adjuvants (collectively referred to herein as "carrier" materials) and, if desired, other active ingredients. The zwitterion form of S-[2-[(1-Iminoethyl)amino]ethyl]-2-methyl-L-cysteine of the present invention may be administered by any suitable route, preferably in the form of a pharmaceutical composition adapted to such a route, and in a dose effective for the treatment intended. The active S-[2-[(1-Iminoethyl)amino]ethyl]-2-methyl-L-cysteine zwitterion and compositions may, for example, be administered orally, intravascularly, intraperitoneally, subcutaneously, intramuscularly or topically.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. The active ingredient may also be administered by injection as a composition wherein, for example, saline, dextrose or water may be used as a suitable carrier.

The amount of therapeutically active compound that is administered and the dosage regimen for treating a disease condition with the compound and/or compositions of this invention depends on a variety of factors, including the age, weight, sex and medical condition of the subject, the severity of the disease, the route and frequency of administration, and the particular compound employed, and thus may vary widely. The pharmaceutical compositions may contain active ingredients in the range of about 0.1 to 2000 mg, preferably in the range of about 0.5 to 500 mg and most preferably between about 1 and 100 mg. A daily dose of about 0.01 to 100 mg/kg body weight, preferably between about 0.5 and about 20 mg/kg body weight and most preferably between about 0.1 to 10 mg/kg body weight, may be appropriate. The daily dose can be administered in one to four doses per day.

S-[2-[(1-Iminoethyl)amino]ethyl]-2-methyl-L-cysteine zwitterion can also be administered by a transdermal device. Preferably topical administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, and sodium lauryl sulfate, among others.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The active ingredients are preferably present in such formulations in a concentration of 0–5 to 20%, advantageously 0.5 to 10% and particularly about 1.5% w/w.

For therapeutic purposes, S-[2-[(1-Iminoethyl)amino]ethyl]-2-methyl-L-cysteine zwitterion is ordinarily combined with one or more adjuvants appropriate to the indicated route of administration. If administered per os, the compound may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The S-[2-[(1-Iminoethyl)amino]ethyl]-2-methyl-L-cysteine zwitterion may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

The invention being thus described, it is apparent that the same can be varied in many ways. Such variations are not to be regarded as a departure from the spirit and scope of the present invention, and all such modifications and equivalents as would be obvious to one skilled in the art are intended to be included within the scope of the following claims. For example, a strong anionic resin could be used, or a weak anionic resin could be employed (see Supelco catalog (part of Sigma-Aldridge)-low pressure ion exchange).

What is claimed is:

1. A method of making a salt of S-[2-[(1-Iminoethyl)-amino]ethyl]-2-methyl-L-cysteine, comprising removing counterions from S-[2-[(1-Iminoethyl)-amino]ethyl]-2-methyl-L-cysteine dihydrochloride in solution by contacting S-[2-[(1-Iminoethyl)-amino]ethyl]-2-methyl-L-cysteine dihydrochloride in solution with an appropriate ion exchange membrane, separating the solution containing S-[2-[(1-Iminoethyl)-amino]ethyl]-2-methyl-L-cysteine from the ion exchange membrane, and contacting the S-[2-[(1-Iminoethyl)-amino]ethyl]-2-methyl-L-cysteine with at least one counterion other than hydrochloride ion.

2. The method of claim 1 wherein at least one counterion is a cation.

3. The method of claim 1 wherein at least one counterion is a anion.

4. The method of claim 1 wherein two stoichiometric counterions are contacted with S-[2-[(1-Iminoethyl)-amino]ethyl]-2-methyl-L-cysteine.

5. The method of claim 4 wherein two stoichiometric counterions are different from one another.

* * * * *